United States Patent [19]
Del Cañizo

[11] Patent Number: 5,931,648
[45] Date of Patent: *Aug. 3, 1999

[54] VACUUM ACTUATED TUBULAR BLOOD PUMPING DEVICE WITH ACTIVE VALUES AND APPLICATION OF THE SAME

[75] Inventor: Juan Francisco Del Cañizo, Madrid, Spain

[73] Assignee: Servicio Regional De Salud, De La Consejeria De Salud De La Comunidad De Madrid, Madrid, Spain

[ * ] Notice: This patent issued on a continued prosecution application filed under 37 CFR 1.53(d), and is subject to the twenty year patent term provisions of 35 U.S.C. 154(a)(2).

[21] Appl. No.: 08/653,837

[22] Filed: May 28, 1996

[30] Foreign Application Priority Data

May 30, 1995 [ES] Spain ................................. 9501070

[51] Int. Cl.⁶ ................................................. F04B 43/08
[52] U.S. Cl. ........................... 417/478; 417/480; 417/510
[58] Field of Search ................................. 417/478, 479, 417/480, 510

[56] References Cited

U.S. PATENT DOCUMENTS

| | | | |
|---|---|---|---|
| 3,007,146 | 11/1961 | Childs | 417/479 |
| 3,478,695 | 11/1969 | Goranson et al. | 103/152 |
| 3,656,873 | 4/1972 | Schiff | 417/395 |
| 4,250,872 | 2/1981 | Tamari | 128/1 D |
| 4,360,324 | 11/1982 | Ohara et al. | |
| 4,409,977 | 10/1983 | Bisera et al. | 417/478 |
| 4,417,861 | 11/1983 | Tolbert | |
| 5,147,187 | 9/1992 | Ito et al. | 417/423.1 |
| 5,171,207 | 12/1992 | Whalen | |
| 5,270,005 | 12/1993 | Raible | 422/46 |
| 5,391,142 | 2/1995 | Sites et al. | 604/4 |
| 5,692,729 | 12/1997 | Harhen | 251/4 |

FOREIGN PATENT DOCUMENTS 403026881  6/1989  Japan ...................... 417/479

*Primary Examiner*—Timothy S. Thorpe
*Assistant Examiner*—Cheryl J. Tyler
*Attorney, Agent, or Firm*—Marshall, O'Toole, Gerstein, Murray & Borun

[57] ABSTRACT

A blood pump having a rigid chamber with a central opening is connected to a vacuum source such that the vacuum source applies a vacuum on an elastic tubular membrane through the opening in the rigid chamber. The blood supply to the chamber is controlled by a first pinch valve disposed on the blood input end and a second pinch valve disposed on the blood output end. In order to pump the blood through the chamber, a vacuum source is applied when the first pinch valve is opened and the second pinch valve is closed to suction blood inside the tubular membrane. Then, the vacuum source ceases to apply a vacuum when the first pinch valve is closed and the second pinch valve is open in order to expel the blood from the tubular membrane. This type of blood pump reduces the formation of platelet aggregates and thrombi, and allows for blood to be more efficiently pumped to the patient.

9 Claims, 1 Drawing Sheet

VACUUM ACTUATED TUBULAR BLOOD PUMPING DEVICE WITH ACTIVE VALUES AND APPLICATION OF THE SAME

The present invention refers to a blood pumping system, tubular in shape, governed by vacuum, in which proper flow direction is obtained by pinch valves placed over the input and output cannulae and which is actuated by a command console that controls all its functions.

FIELD OF THE INVENTION

This invention may be applied within the industry dedicated to the manufacture of medicinal apparatus.

BACKGROUND OF THE INVENTION

There are several situations in medicine where it is necessary to pump blood, by means of an artificial device.

1. During open heart surgery by means of what is called the extracorporeal circulation (ECC).
2. In acute cardiac or respiratory failure in which the so-called extracorporeal membrane oxygenator is used (ECMO).
3. In patients with profound ventricular failure in which the so-called artificial ventricles may be used.
4. In Hemodialysis with the so-called artificial kidney and in the new apheresis systems.

All these cases need to use a device which pumps blood, with the following features:

1. Be effective from a hemodynamic point of view, i.e. they must be capable of supplying an appropriate blood flow in all the conditions which may arise within the specific application.
2. The mechanical effort which the blood forming elements are submitted to, especially red globules, must be minimal, i.e. homolysis must not arise.
3. They must not produce any formation of added plaques nor thrombi which may be released and lead to embolies in the patient.

Optimization of the blood pumps depends on four types of solutions.

A. Solutions which help to reduce the formation of platelet aggregates and thrombi, basically aimed at being designed so as to avoid areas of blood stagnation.

B. Solutions aimed at reducing the lesions produced in the blood forming elements.

C. Solutions aimed at reducing the cost of the device in order to extend its application field.

D. In some applications such as the use of artificial ventricules there must be solutions to improve the filling up of the blood chamber.

SUMMARY OF THE INVENTION

According to the invention, a tubular shaped blood pump device includes an elastic tubular membrane disposed in a rigid chamber, a first pinch valve located at an input cannula of the membrane and a second pinch valve located at an output cannula of the membrane. The pinch valves and a vacuum source are connected to, and controlled by, a command console. The tubular membrane expands when a vacuum is applied thereon with the first pinch valve closed and the second pinch valve open, which suctions blood into the tubular membrane. When vacuum application ceases, the first pinch valve is closed and the second pinch valve is opened, giving rise to expulsion of blood out of the tubular membrane.

DESCRIPTION OF THE PREFERRED EMBODIMENTS

Figure 1:
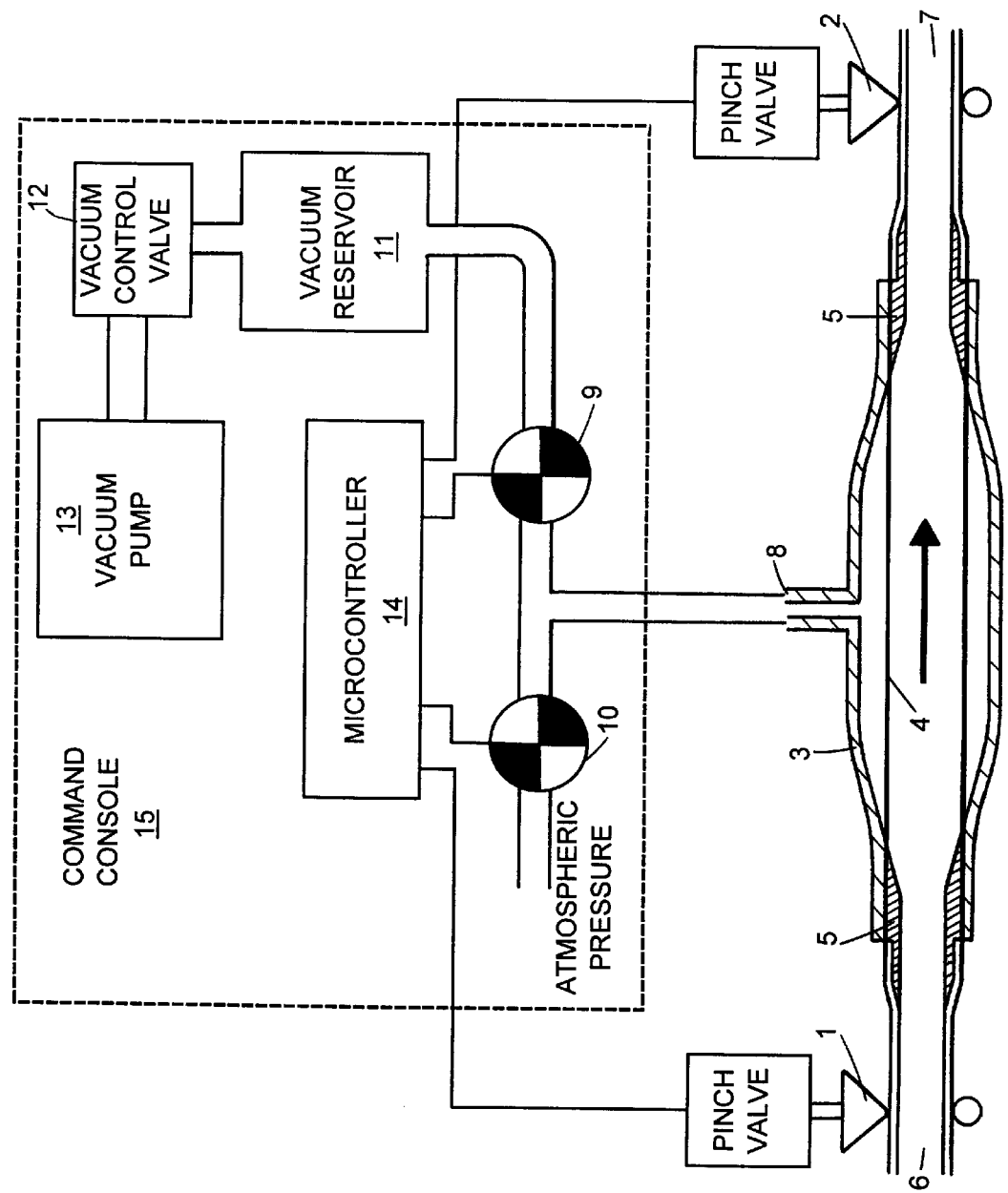
FIG. 1 is a schematic view of a tubular blood pump according to the invention.

A vacuum actuated blood pumping device includes a blood chamber comprising a tubular elastic membrane having an initial shape with a constant diameter throughout the length of the membrane, the membrane having a blood input end and a blood output end. Connection pieces are disposed at the blood input and blood output ends. A flexible input cannula is coupled to the input connection piece and a flexible output cannula is coupled to the output connection piece. The membrane is axially installed inside a rigid chamber having a central portion, the rigid chamber surrounding the tubular membrane from the blood input end to the blood output end, and having an opening at the central portion to provide a connection with a vacuum source for applying vacuum upon the tubular membrane through the opening. In some applications, especially those related to artificial ventricles, a second, complementary chamber may be added to optimize filling, at the pump entrance.

The majority of blood pump devices in the art today are based on the compression of a chamber, either by means of a gas, or by means of rollers in order to reduce its dimensions and provoke liquid propulsion. In this device a new concept is used. The propulsion chamber is an elastic tube with thin walls and with constant diameter throughout the length of the tube, which is placed on the inside of a rigid chamber.

Vacuum can be applied to this rigid chamber by means of a vacuum source controlled by the console. Vacuum applied to the elastic tubular chamber forces the chamber to expand in a very homogeneous way, thereby avoiding wrinkles capable of producing stagnation points. When the console switches off the vacuum and connects the rigid chamber to the atmospheric pressure, the ensuing elastic recuperation of the blood-chamber walls gives the necessary impulse to the blood. Systole is completely passive in this device.

The use of vacuum instead of pressurized gas offers another advantage. In case of membrane leakage, gas cannot enter into the blood circulation because pressure in the blood chamber is always higher than in the pneumatic chamber. This eliminates the risk of gas emboli formation in the patient.

The external pinch valves according to the invention may be activated pneumatically, electrically, electromagnetically, or mechanically, depending on the use of the device in a specific application.

The use of active external pinch valves reduces dramatically the cost of the device compared with those that utilize classical mechanical valves. Classical mechanical valves used in these kind of applications are too expensive for use in applications like hemodialysis or ECC. Moreover the utilization of this kind of pinch valve makes very uniform the shape of the cannulae, and the cannulae can be adapted for a wide variety of applications. For example, in pediatric and hemodialysis applications the cannulae used are of a diameter much smaller than 16 mm, the diameter used in smaller mechanical valves.

A device according to the invention minimizes the stress over the blood cells, because the only stress source is the closing of the pinch valves, which occurs only at two points. In contrast, roller pumps squeeze continuously the tube contents, and open mechanical valves present some surfaces that may alter blood flow. In an embodiment according to the invention, when the pinch valve opens, the inner section of the tube is uniform.

In some applications, such as those in which it is necessary to manage high flows, like mechanical circulatory support systems (MCSS), it may be helpful to add an elastic chamber in the input cannula, in order to make filling the pump easier. This elastic chamber could be of the same type as the blood chamber. The elasticity of the chamber can be modified by varying the vacuum level applied to the elastic chamber, depending on the working conditions.

In this type of applications safety is also an essential factor.

The design of this pump allows for connecting two pumps in parallel form so that one of them acts as a security mechanism with the two pinch valves closed whilst inactive, being able to automatically operate should the need arise if the main pump fails.

The design of the pump also allows for flow inversion, simply inverting the sequence of aperture of the pinch valves, which is not possible in those devices which use passive mechanical valves.

FIG. 1 shows a cross section of the blood pumping device, with the control console shown schematically.

The present application refers to a tubular shaped blood pump, actuated by vacuum in which the flow direction is obtained by pinch valves placed over the input and output cannulae instead of mechanical valves and which is actuated by a command console to control all its functions. The single drawing represents a transversal section of the device.

1. Input pinch valve (i.e., entrance stenosizer);
2. Output pinch valve (i.e., exit stenosizer);
3. Rigid chamber;
4. Elastic tubular membrane;
5. Connection pieces (i.e., nozzle connection pieces);
6. Flexible input cannula (i.e., elastic entrance nozzle);
7. Flexible output cannula (i.e., elastic exit nozzle);
8. Command console connection (i.e., connection for vacuum);
9. Vacuum electrovalve;
10. Open air electrovalve;
11. Vacuum reservoir;
12. Vacuum level control valve;
13. Vacuum pump;
14. Microcontroller; and
15. Command console.

OPERATION

FIG. 1 shows a cross section of the device. The vacuum line connects the pneumatic chamber with the control console.

During the filling of the pump, the control console connects the line 8 to vacuum, causing the membrane 4 to expand. At the same time the control console or command console 15 causes the output pinch valve 2 to close and the input pinch valve 1 to open. As a result, the blood then comes through the input cannula 8, filling the blood chamber.

During the systolic period, the control console connects the line 8 with the atmospheric pressure. At the same time the control console causes the input pinch valve 1 to close and the output pinch valve 2 to open. Consequently, the elastic recuperation of the membrane free of the vacuum drives the blood through the output cannula 7.

I claim:

1. A vacuum actuated blood pumping device comprising:
   a blood chamber comprising a tubular elastic membrane having an initial shape with a constant diameter throughout the length of the membrane, the membrane having a blood input end and a blood output end;
   an input connection piece disposed at the blood input end;
   an output connection piece disposed at the blood output end;
   a flexible input cannula coupled to the input connection piece;
   a flexible output cannula coupled to the output connection piece;
   the membrane being axially installed inside a rigid chamber having a central portion, the rigid chamber surrounding the tubular membrane from the blood input end to the blood output end, and having an opening at the central portion to provide a connection with a vacuum source for applying vacuum upon the tubular membrane through the opening;
   a first active pinch valve disposed on the flexible input cannula adjacent the blood input end;
   a second active pinch valve disposed on the flexible output cannula adjacent the blood output end;
   a command console including a vacuum source, the command console connected to and controlling the pinch valves for pumping blood through the membrane, the blood pumping device having two operating conditions,
   (a) a first condition wherein the tubular membrane expands diametrically when the vacuum source applies vacuum thereupon with the first pinch valve being open and the second pinch valve being closed, thus giving rise to suction of blood inside the tubular membrane; and
   (b) a second condition wherein the tubular membrane substantially returns to its initial shape when the vacuum source ceases to apply vacuum thereupon with the first pinch valve being closed and the second pinch valve being open, thus giving rise to expulsion of blood outside the tubular membrane.

2. The blood pumping device of claim 1 wherein the command console further comprises:
   a vacuum reservoir connected to the vacuum source through a vacuum level control valve; a vacuum electrovalve connected to the vacuum reservoir; an open air electrovalve connected to the vacuum electrovalve, the vacuum electrovalve and open air electrovalve connected to the rigid chamber through the opening; and
   a microcontroller connected to the vacuum electrovalve, open air electrovalve, and first and second pinch valves.

3. The blood pumping device of claim 2 wherein during the first operating condition the vacuum electrovalve is opened and the open air electrovalve is closed and wherein during the second operating condition the vacuum electrovalve is closed and the open air electrovalve is opened.

4. The blood pumping device of claim 1 wherein the pinch valves are activated pneumatically, electrically, electromagnetically, or mechanically.

5. The blood pumping device of claim 1 wherein the pump is adapted for use in a hemodialysis, hemofiltration, or apheresis system.

6. The blood pumping device of claim 1 wherein the pump is adapted for use in an extracorporeal membrane oxygenator (ECMO).

7. The blood pumping device of claim 1 wherein the pump is adapted for use in an extracorporeal circulation system.

8. The blood pumping device of claim 1 wherein the pump is adapted for use as an artificial ventricle in a system of mechanical circulatory assistance.

9. The blood pumping device of claim 1 wherein the pump is adapted for use in a medical system requiring a pump that produces little hemolysis and low production of additional plaques and clots.

* * * * *